(12) United States Patent
Leroy et al.

(10) Patent No.: US 11,899,144 B2
(45) Date of Patent: Feb. 13, 2024

(54) METHOD FOR IMPROVING THE POSITION RESOLUTION OF A POSITRON SOURCE DURING POSITRON EMISSION TOMOGRAPHY

(71) Applicant: CZECH TECHNICAL UNIVERSITY IN PRAGUE, INSTITUTE OF EXPERIMENTAL AND APPLIED PHYSICS, Prague (CZ)

(72) Inventors: Claude Leroy, Quebec (CA); Stanislav Pospíšil, Prague (CZ)

(73) Assignee: CZECH TECHNICAL UNIVERSITY IN PRAGUE, INSTITUTE OF EXPERIMENTAL AND APPLIED PHYSICS, Prague (CZ)

( * ) Notice: Subject to any disclaimer, the term of this patent is extended or adjusted under 35 U.S.C. 154(b) by 276 days.

(21) Appl. No.: 17/244,054

(22) Filed: Apr. 29, 2021

(65) Prior Publication Data

US 2021/0263173 A1 Aug. 26, 2021

Related U.S. Application Data

(63) Continuation of application No. PCT/CZ2019/000052, filed on Oct. 24, 2019.

(30) Foreign Application Priority Data

Oct. 31, 2018 (CZ) .............................. PV 2018-592

(51) Int. Cl.
*A61B 6/03* (2006.01)
*G01T 1/29* (2006.01)
*A61B 6/00* (2006.01)

(52) U.S. Cl.
CPC ............ *G01T 1/2985* (2013.01); *A61B 6/037* (2013.01); *A61B 6/5211* (2013.01); *G01T 1/2992* (2013.01)

(58) Field of Classification Search
CPC .............................. A61B 6/037; A61B 6/5711
See application file for complete search history.

(56) References Cited

U.S. PATENT DOCUMENTS 4,531,058 A 7/1985 Burnham et al.
2003/0048864 A1 3/2003 Akers
(Continued)

FOREIGN PATENT DOCUMENTS

RU 2599192 C2 10/2016

OTHER PUBLICATIONS

Torrisi et al. Doppler-broadening of positron annihilation in a biological environment, The Quarterly Journal of Nuclear Medicine, vol. 41, pp. 18-24 (Year: 1997).*

(Continued)

*Primary Examiner* — David P Porta
*Assistant Examiner* — Shun Lee
(74) *Attorney, Agent, or Firm* — Panitch Schwarze Belisario & Nadel LLP

(57) ABSTRACT

The investigated object containing a source of positrons is placed into a system of n position and energy-sensitive gamma radiation detectors ($D_i$), each having detection elements ($D_{ijk}$), where one of a pair of annihilation photons interacts in the detection element ($D_{1jk}$) and the other interacts in another detection element ($D_{2jk}$). The detectors store the coordinates of simultaneously affected detector elements, the time of interactions and the energies $E_1$ and $E_2$ of the annihilation photons. The recorded events in the detection elements ($D_{1jk}$) and ($D_{2jk}$) leads to recognition of individual pairs of annihilation photons. An analysis is performed of the registration of the photons by the detection elements ($D_{1jk}$) and ($D_{2jk}$) with energies in the interval from 507 keV to 513 keV to obtain an approximate spatial depiction of positions of positron annihilation and, registra- (Continued)

tion of the photons from the positron annihilation with significantly Doppler shifted energies outside of that interval.

11 Claims, 3 Drawing Sheets

(56) References Cited

U.S. PATENT DOCUMENTS

| | | |
|---|---|---|
| 2008/0067372 A1 | 3/2008 | Hunt et al. |
| 2010/0230602 A1 | 9/2010 | Scheins |
| 2018/0144513 A1 | 5/2018 | Liu et al. |

OTHER PUBLICATIONS

International Search Report (PCT/ISA/210) and Written Opinion (PCT/ISA/237) dated Feb. 17, 2020, by the Visegrad Patent Institute as the International Searching Authority for International Application No. PCT/CZ2019/000052.

\* cited by examiner

METHOD FOR IMPROVING THE POSITION RESOLUTION OF A POSITRON SOURCE DURING POSITRON EMISSION TOMOGRAPHY

TECHNICAL FIELD

The invention concerns the method for improving the position resolution of a positron source during positron emission tomography using the Doppler effect.

Present State of the Art

Positron Emission Tomography (PET) is an imaging method based on detection of gamma ray photons, resulting from the annihilation of positrons emitted by beta plus radioactive emitters in matter. If the positron annihilates with an electron, its extinction is accompanied by creation of two "annihilation" photons, each of which has the energy of 511 keV in corresponding Centre of Mass System (CMS), flying off in opposite directions from each other. A coincidence detection system that records the direction of flights of these photons is necessary during PET. The present state of knowledge in the field of the invention is summarised in a publication of W. Moses, "Fundamental Limits of Spatial Resolution in PET", Nucl. Instr. Meth. Phys. Res. A, 2011 Aug. 21, 648 Supplement 1, S236-S240. He explicitly specifies the insurmountable limits of the spatial resolution in measurement of a distribution of positron emitters in the investigated objects, which results of the range of positrons in the object environment. In practice, it states that the position, where the annihilation photons were created, differs from the position, where the parent nucleus of the beta plus radioactive isotope that emitted the positron was located. This leads to blurring of the image of investigated parent nuclei distribution, whose size depends on the type of radioisotope used. The work documents that the aforementioned blurring given in the form of FWHM is for the series of radionuclides used in PET in the range from 0.54 mm for $^{18}$F up to 6.14 mm for $^{82}$Rb. The authors C. S. Levin and E. J. Hoffman came to similar conclusions in their work "Calculation of positron range and its effect on the fundamental limit of positron emission tomography system, spatial resolution", Phys. Med. Biol. 44 (1999) 781-799. Both of the works deal with facts that the annihilation of positrons in matter does not correspond to the position of the positron source, though the determination of the source is the objective of any PET, especially for imaging in medicine. Positrons emitted by a source predominantly annihilate after achieving equilibrium with thermal motion of electrons in matter. Thus, the place in which the annihilation photons were created, which is in reality determined in PET, does not correspond to the position from which the original positron was emitted. In addition to this, there have been many attempts done to localise the positron source in the investigated object. These include the method based on the measurement of the time-of-flight of annihilation photons from the place of their creation to the detector. This method, however, does not resolve the problem caused by positron annihilation out of the position of the positron source, even though it can otherwise be effectively used for identification the undesired scattering of annihilation photons in the object environment. In parallel, some works dealing with investigation of the in-flight annihilation of positrons in materials with the use of the Doppler effect, which influences the energies of the annihilation photons, have also been published. This issue is described in great detail in, for example, the publication from Čižek et al, "Investigation of positron annihilation-in-flight using a digital coincidence Doppler broadening spectrometer", New Journal of Physics 14 (2012) 035005 (18 pp) 2 Mar. 2012. The work, however, does not address the questions of where the positrons originated and/or annihilate. Only the patent documents specified below deal with the issue of the Doppler effect influencing energies of photons arising from the annihilation of positrons in flight. The document US 2008/0067372 concerns with the positron annihilation process for recognition of defects in materials using a beam of energetic particles producing in a material positrons, which annihilate there revealing presence of the defects by measuring the broadening of measured energies of annihilation photons, from which the number of defects in the examined material is deduced. However, the places of positron creation are not specified. A methodologically similar use of the Doppler effect in medical diagnostics is the subject of patent document RU 2599192, in which the method for determining the tissue density by means of positrons implanted into the investigated tissue from outside is described. The given method is based on dependence of the positron velocity on the tissue density. However, neither of the documents described above deal with the tomographic use of positron annihilation. Though, the process of the positron annihilation is used, the given methods do not determine the place of positron creation nor the place of their annihilation in matter, which is the basic objective of the PET. Thus, this is an application entirely different from PET. Even though the basic principles of using positron annihilation for PET purposes is known reasonably well since a long time, there has not yet been proposed improvement of PET by means of contemporary available detectors allowing precise measurement of Doppler shifts of energies of annihilation photons in parallel with precise measurement of position and time of photon arrivals to the detector for the determination of the positron source position in the examined matter. The general opinion still is, that the range of positrons in matter remains the principle obstacle preventing the precise determination of the positron source position by means of the PET. However, the several biomedical applications of PET, currently in particular for the imaging of vitally important organs in human medicine and for the small animal research imaging, urgently require PET with increased accuracy.

SUMMARY OF THE INVENTION

The method of improvement of the resolution of the positron source position in an object investigated by means of positron emission tomography enhanced by measurement of Doppler shifts of annihilation photon energies resulting from positron annihilation in flight, consists from the following steps:

First, the investigated object, containing a source of positrons that annihilate through the production of pairs of annihilation photons, is placed into a system of n position and energy-sensitive detectors of gamma radiation each consisting of a system of detection elements, whose placement is described by a three-dimensional coordinate system. Subsequently, once one of the pairs of annihilation photons interacts in the first of the affected detection elements and the second one from that pair of annihilation photons interacts in the second of the affected detection elements, which record the data about such events consisting of the coordinates of the positions of the interactions in the three-dimensional coordinate system describing the positions of the detection elements in relation to the investigated object, the time of interactions of the annihilation photons with the affected detection elements, and energies $E_1$ and $E_2$, which the individual photons deposited in the affected elements. All data of these events are transferred through an interface to a computer that serves to control the detectors and detection elements, and to assignment of the events recorded in the detection elements to the individual pairs of annihilation photons according to the time of their interactions in the detector elements. Here the events are subsequently analysed for the purpose of the reconstruction of a three-dimensional depiction of the spatial distribution of the positron emitters in the investigated object. The analysis concerns both, the coincidental events of registrations of the annihilation photons with energies in the interval from 507 keV to 513 keV to obtain the spatial depiction of the positions of positron annihilations, which approximates the position of the positron source, and the coincidental events of registrations of the annihilation photons with significantly Doppler shifted energies outside of that interval, which simultaneously fulfill the condition that the sum of the measured energies of these photons is, within the energy resolution of the affected detection elements, equal 1022 keV in CMS. This, according to the kinematics of positron annihilation, proves, that the positrons annihilated in flight closer to the position of the positron source, and thus allows to refine the determination of the positron source position in the investigated object initially obtained from the aforementioned approximated depiction of the source positions taking into account just the annihilation photons with energies from 507 keV to 513 keV. The refined reconstruction of positions of the positron sources in an investigated object is preferably carried out with the help of the kinematics of positron annihilation with electrons in flight on the basis of the measured energies of the individual pairs of concurrently occurring annihilation photons and the coordinates of the positions of their registration in the affected detection elements in the three-dimensional coordinate system according to the relativistic relations ensuing from the energy and momentum conservation laws, $$\cos\theta = mc^2[(E_1+E_2)/E_1E_2]-1, \text{ where } E_1E_2=(\frac{1}{4})[(E_1+E_2)^2-(E_1-E_2)^2],$$

$$\cos\phi = (E_1-E_2\cos\theta)/[(E_1+E_2)(E_1+E_2-2mc^2)]^{1/2},$$

$$T_+ = E_1+E_2-2mc^2,$$

where $E_1$ and $E_2$ are the measured energies of photons resulting from annihilation of the positron with kinetic energy $T_+$ with an electron that was at rest or in thermal motion, that are influenced by the Doppler shift. $E_1$ pertains to the photon with the Doppler shift towards higher energy, $E_2$ towards lower energy. The $mc^2$ gives the rest energy of the positron or electron, where symbol m is the rest mass of them and c is the velocity of light, $p_+$ represents the momentum vector of the annihilating positron, $p_1$ and $p_2$ represent the momentum vectors of each annihilation photon from the pair, $\theta$ indicates the angle expressing the non-collinearity of those photons, $\phi$ the angle between the directions of vectors $p_1$ and $p_+$. The positions of positron annihilations in such events are determined from the coordinates of the affected detection elements, which measure $E_1$ and $E_2$ of the relevant coinciding annihilation photons, and from the calculated values of $T_+$ and the angles $\theta$ and $\phi$. This is then followed by the basic relations that describe the change of energies of the annihilation photons in the case of the annihilation of positrons in flight:

$$E_1 = ((T_+ + 2mc^2)\cos\theta + cp_{+y})/(1+\cos\theta),$$

$$E_2 = ((T_+ + 2mc^2) - cp_{+y})/(1+\cos\theta),$$

where $p_{+y}$ is the component of momentum $p_+$ in the direction of the flight of the annihilation photon with the energy of the Doppler shift towards higher energy with respect to 511 keV for the first photon. The component $cp_{+y}$ is equal to $cp_+\cos\phi$. The component $cp_{+y}$ is also equal to $\Delta E_1 = E_1 - mc^2$ and in accordance with the law of the conservation of energy also to $\Delta E_2 = mc^2 - E_2$ in terms of size, which corresponds to the energy of the second photon shift towards the energy lower than 511 keV.

From the formulae given above, we can also derive the following:

$$E_1 + E_2 = T_+ + 2mc^2$$

$$E_1 - E_2 = \Delta E = \Delta E_1 + \Delta E_2 = (2cp_{+y} - (T_+ + 2mc^2)(1-\cos\theta))/(1+\cos\theta) = (2\Delta E_1 - (T_+ + 2mc^2)(1-\cos\theta))/(1+\cos\theta),$$

where $\Delta E_1 = cp + \cos\phi = \{[T_+(T_+ + mc^2)]^{1/2}\}\cos\phi$

As soon as we measure $E_1$ and $E_2$, the energy shifts $\Delta E_1$ and $\Delta E_2$ are also known. The kinetic energy of the positrons $T_+$ as well as the angles $\theta$ and $\phi$ can subsequently be determined from these independently measured quantities, $$\cos\theta = mc^2[(E_1+E_2)/E_1E_2]-1, \text{ where } E_1E_2=(\frac{1}{4})[(E_1+E_2)^2-(E_1-E_2)^2],$$

$$\cos\phi = (E_1-E_2\cos\theta)/[(E_1+E_2)(E_1+E_2-2mc^2)]^{1/2},$$

$$T_+ = E_1+E_2-2mc^2,$$

which is sufficient for the complete reconstruction of the positions where the positron in flight annihilation occurred. It follows from the above given information that the reconstruction of positions of positron annihilations is based on the energies of $E_1$ and $E_2$ of annihilation photons measured in coincidence by affected detection elements in which the photons from the relevant pair interacted, and from the calculated values of $T_+$ and angles $\theta$ and $\phi$. The chosen coordinate system corresponds to the conventions according to the invention, where the direction of the flight of the photon with the higher energy $E_1$ determines the orientation of the axis y for the first affected detection element and where we know the position of the second affected detector. Since such a vector diagram can be reconstructed for each coincidental event of the registration of a pair of annihilation photons of the affected detection element, 3D coordinates of the positions in which the positrons were annihilated in flight can be found as an intersection point of the y axes, which corresponds to each of the coincidental detections of Doppler shifted annihilation photons.

The described Doppler enhancement PET becomes particularly effective if the positrons originating in the studied object have energies greater than 10 keV. The $^{22}$Na, $^{18}$F, $^{94}$Tc, $^{11}$C, $^{13}$N, $^{44}$Sc, $^{15}$O, $^{14}$O, $^{68}$Ga, $^{124}$I, $^{10}$C, $^{152}$Tb, $^{86}$Y, $^{76}$Br, $^{82}$Sr/$^{82}$Rb beta plus radionuclides are fulfilling this condition. For the reconstruction, it is advantageous if the coincidental events of the registration of the pairs of annihilation photons with significantly Doppler shifted energies obtain for refining the depiction of the spatial distribution of positron sources in the investigated object greater weight the greater are the Doppler shifted energies. The equipment for refining of the determination of the position of the positron sources in an object by the proposed modification of positron emission tomography consists of a system of n position and energy-sensitive detectors of gamma rays consisting of a system of detection elements, whose placement is described by a three-dimensional coordinate system, whereby the detection elements are connected through an interface to a computer, which is used to control the detectors and detection elements and read and analyse the signals from them for the purpose to reconstruct of a three-dimensional depiction of the spatial distribution of the positron source in the investigated object. The pixel semiconductor detectors with pixel semiconductor sensors sensitive spectrally to gamma rays can be advantageously used as their system of pixels corresponds to the system of required detection elements. The pixel semiconductor sensors with a high effective atomic number of $Z_{eff}$ as CdTe and CdZnTe are among the preferable semiconductor materials. Specifically, the use of hybrid pixel detectors with pixels of about 55 microns or smaller, can be advantageously used for improving of PET resolution. The interface for controlling the detectors and detection elements and for reading of the signal from them can be chosen from the group of universal serial bus (USB), Ethernet and PCI interfaces.

DESCRIPTION OF THE FIGURES ON THE DIAGRAMS

EXAMPLES OF IMPLEMENTING THE INVENTION

Example 1

Figure 1:
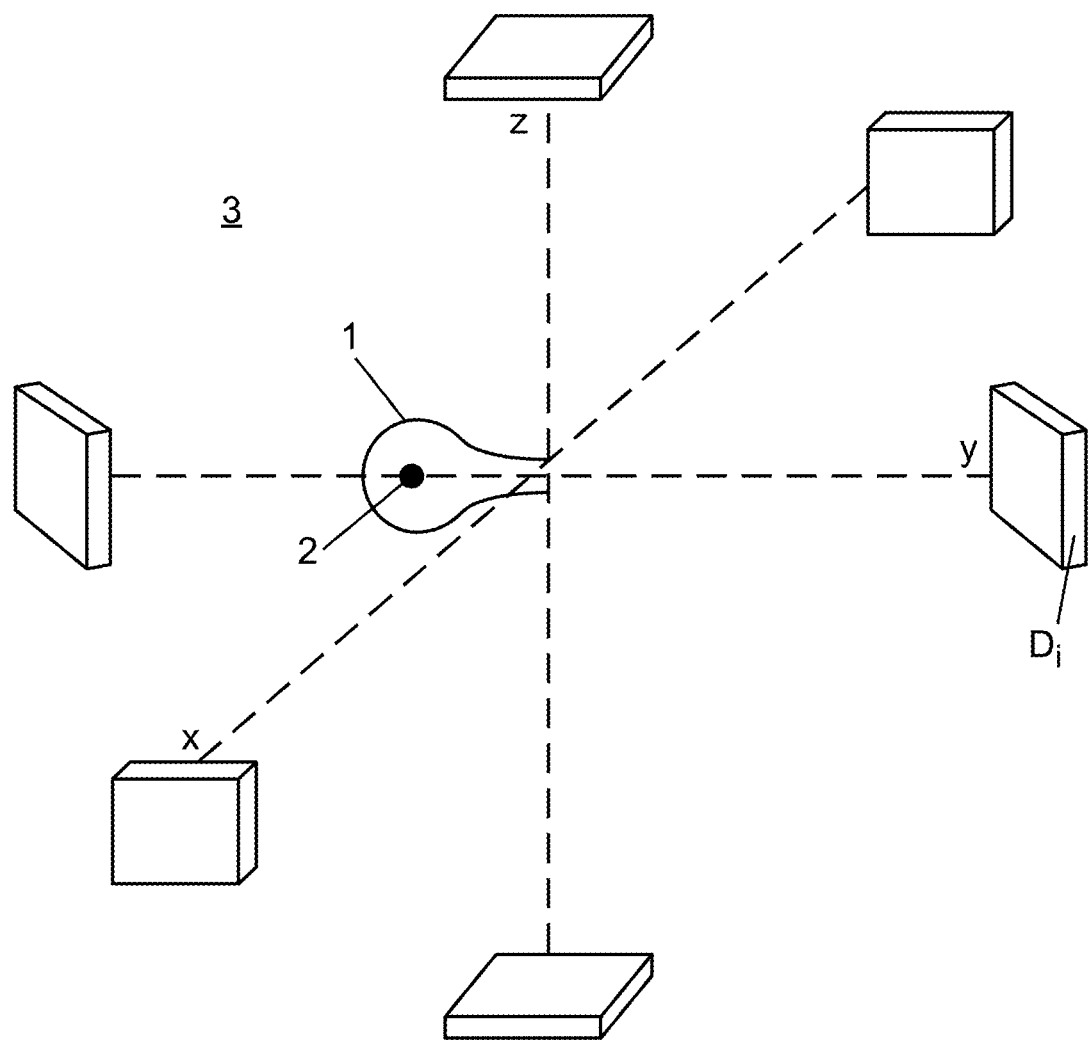
FIG. 1 depicts the schematic arrangement of the system of position and energy-sensitive detectors of gamma rays.
Figure 2:
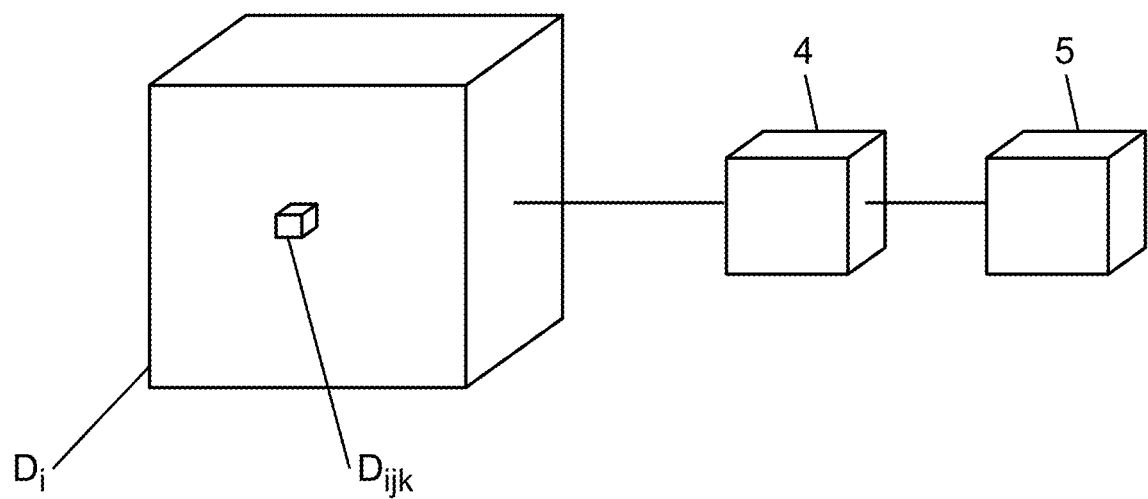
FIG. 2 depicts a detailed view of a detection element, which is part of the position and energy-sensitive detectors of gamma rays, which is connected through an interface to the control and evaluation computer.
Figure 3:
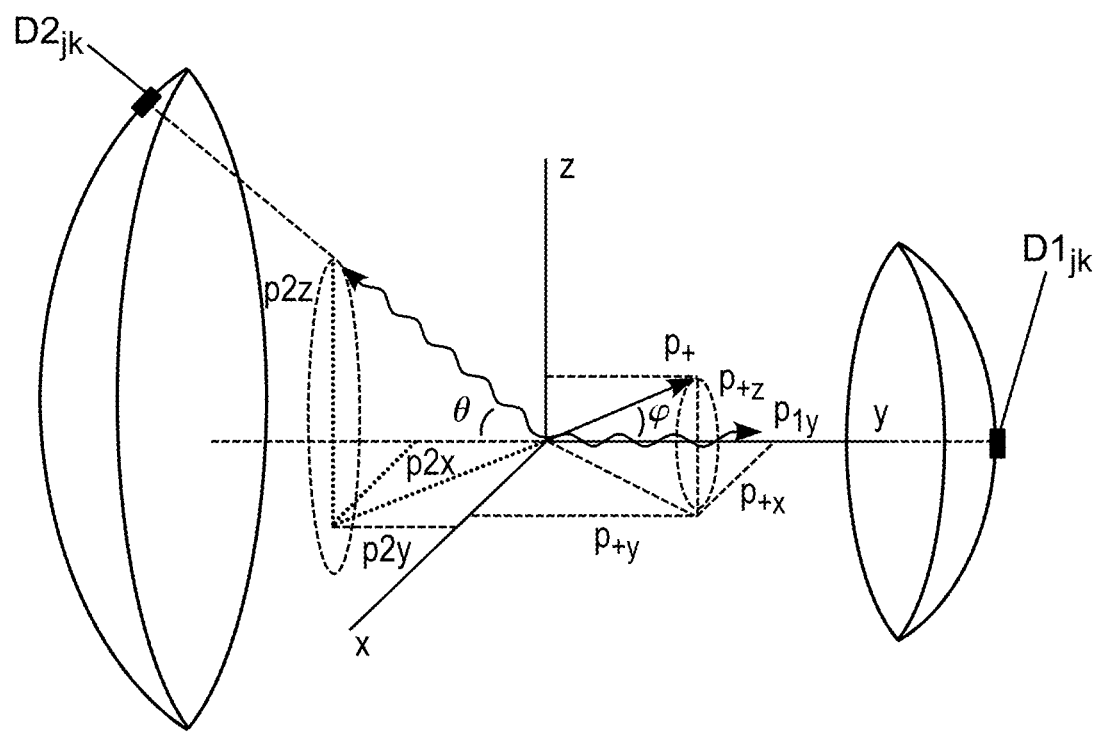
FIG. 3 represents the vector scheme depicting the kinematics of the annihilation of positrons in flight within the coordinate system corresponding to the convention according to the invention with affected detection elements indicated.

First the studied object 1 containing a source 2 of positrons, which annihilate primarily through the production of a pair of annihilation photons, was placed into a system 3 of n position and energy-sensitive detectors $D_i$ of gamma radiation comprised of a system of detection elements $D_{ijk}$, whose mutual placement is described by a three-dimensional coordinate system. Subsequently, one of the pairs of annihilation photons interacted in the first of the affected detection elements $D_{1jk}$ and the second one of this pair of annihilation photons interacted in the second of the affected detection elements $D_{2jk}$, which then recorded the data about such events, which are the coordinates of the positions of the interactions in the three-dimensional coordinate system of the description of the positions of the detection elements $D_{ijk}$ in relation to the studied object 1, the time of the annihilation photons' interaction with the detection elements $D_{ijk}$ and energies $E_1$ and $E_2$, which the individual photons from the pair left in the affected elements $D_{ijk}$ and $D_{2jk}$. Then, the mutual allocation of the recorded events in the detection elements $D_{1jk}$ and $D_{2jk}$ to the individual pairs of annihilation photons was performed using the coincidence method. All the aforementioned events were subsequently, through an interface 4 used to control the detectors $D_i$ and detection elements $D_{ijk}$ and for reading the signal from them, transmitted to a control and evaluation computer 5, in which they were analysed for the purpose of the reconstruction of a three-dimensional depiction of the spatial placement of the positron emitters in the source 2 of the positrons in the studied object 1. The analysis concerned both, the coincidental events of the registrations of the annihilation photons with energies in the interval from 507 keV to 513 keV to obtain spatial depiction of the positions of positron annihilations and the coincidental events of the registrations of the annihilation photons with significantly Doppler shifted energies outside of that interval, which simultaneously fulfill the condition that the sum of the measured energies of these photons is, within the energy resolution of the affected detection elements $D_{ijk}$, equal 1022 keV in CMS. This corresponds to the positron annihilation in flight in the closer vicinity of the position of its creation, which permits to refine determination of positron sources in the studied object initially obtained from the aforementioned approximated spatial depiction of the sources based only on photons with energies from 507 keV to 513 keV.

Example 2

The studied object 1 containing a source 2 of positrons was examined similarly as in Example 1, only differing in the method for reconstructing the position of the sources 2 of positrons in the studied object 1 using the kinematics of positron annihilation with electrons in flight on the basis of the measured energies of the individual pairs of concurrently occurring annihilation photons and the coordinates of the positions of their registration in the affected detection elements $D_{1jk}$ and $D_{2jk}$ in the three-dimensional coordinate system according to the relativistic relations ensuing from the laws of the conservation of energy and momentum, $$\cos \theta = mc^2[(E_1+E_2)/E_1E_2]-1, \text{ where } E_1E_2 = (\tfrac{1}{4})[(E_1+E_2)^2-(E_1-E_2)^2],$$

$$\cos \phi = (E_1 - E_2 \cos \theta)/[(E_1+E_2)(E_1+E_2-2mc^2)]^{1/2},$$

$$T_+ = E_1 + E_2 - 2mc^2,$$

where $E_1$ and $E_2$ are the measured energies of the pair of annihilation photons that are influenced by the Doppler shift as a result of the annihilation of the positron with the kinetic energy $T_+$ with an electron that was at rest or in thermal motion. $E_1$ pertains to the photon with the Doppler shift towards higher energy, $E_2$ towards lower energy. The symbol m gives the rest mass of the positron or electron, c is the speed of light, $p_+$ represents the momentum vector of the positron at the moment of annihilation, $p_1$ and $p_2$ represent the momentum vectors of each annihilation photon from the pair, $\theta$ indicates the angle expressing the non-collinearity of these photons, $\phi$ is the angle between the directions of the vectors $p_1$ and $p_+$, while the positions of positron annihilations in such events are determined from the coordinates of the affected detection elements $D_{1jk}$ and $D_{2jk}$, which in coincidence measure $E_1$ and $E_2$ of the relevant annihilation photons, and from the calculated values of $T_+$ and the angles $\theta$ and $\phi$. For the reconstruction it is most advantageous if the coincidental events of the registration of the pairs of annihilation photons with significantly Doppler shifted energies obtain for refining the depiction of the distribution of positron sources in the investigated object greater weight once the Doppler shifts of the energies are greater. It was experimentally verified that the proposed approach is suitable if the positrons originating in the studied object have energies greater than 10 keV. It is especially significant in the event that the sources of the positrons are beta plus radionuclides with high energies of beta plus decay selected from the following group $^{22}$Na, $^{18}$F, $^{94}$Tc, $^{11}$C, $^{13}$N, $^{44}$Sc, $^{15}$O, $^{14}$O, $^{68}$Ga, $^{124}$I, $^{10}$C, $^{152}$Tb, $^{86}$Y, $^{76}$Br, $^{82}$Sr/$^{82}$Rb, which leads to such a significant blurring of PET because of the large range of the positrons in the studied object 1 that the method of improving of the positron source depiction according to the invention is desirable and effective.

Example 3

The exemplary equipment for determination of the position of the positron sources in an investigated object by means of advanced positron emission tomography according to the invention is comprised of a system 3 of n position and energy-sensitive detectors $D_i$ of gamma radiation consisting of a system of detection elements $D_{ijk}$. Their mutual placement is described by a three-dimensional coordinate system. The detectors $D_i$ and detection elements $D_{ijk}$ are connected through an interface 4 for their control and for reading the signal from them with a control and evaluation computer 5, which is also used for the analysis of the signal from the detectors for the purpose of reconstruction of a three-dimensional depiction of the spatial placement of positron emitters in the source 2 of the positrons in the studied object 1. In practice, for the implementation of the invention, the hybrid pixel detectors with a CdTe or CdZnTe pixel semiconductor sensors have proven most effective as the detectors $D_i$, where the system of pixels with dimensions of 55 micrometers created on them corresponds to the system of detection elements $D_{ijk}$ pursuant to the invention. It has been verified that a suitable interface 4 for the control of these pixel detectors a and detection elements $D_{ijk}$ and for reading the signal from them is USB, Ethernet or PCI.

INDUSTRIAL APPLICABILITY

The method according to the invention is usable in several biomedical PET applications, currently especially in particular for the imaging of vitally important organs in human medicine and during the research of small animals. Other perspective applications are in non-destructive material research.

The invention claimed is:

1. The method of improvement of the positron source position determination in an object investigated by the positron emission tomography utilizing Doppler effect comprises the following steps:

the investigated object containing a source of positrons, which annihilate through the production of pairs of annihilation photons, is placed into a system of n position and energy-sensitive detectors ($D_i$) of gamma radiation each comprised of a system of detection elements ($D_{ijk}$), whose placement is described by a three-dimensional coordinate system, where one of the pairs of annihilation photons interacts in the first of the affected detection elements ($D_{1jk}$) and the second one of this pair of annihilation photons interacts in the second of the affected detection elements ($D_{2jk}$), which then record the data about such events consisting of the coordinates of positions of the interactions in the three-dimensional coordinate system describing the positions of the detection elements ($D_{ijk}$) in relation to the investigated object, the time of interactions of the annihilation photons with the affected detection elements ($D_{1jk}$) and ($D_{2jk}$), and energies $E_1$ and $E_2$, which the individual photons from the pair left in the affected elements ($D_{1jk}$) and ($D_{2jk}$), and then the mutual assignment of the events recorded in the detection elements ($D_{1jk}$) and ($D_{2jk}$) to the individual pairs of annihilation photons is performed according to their time of interactions and the events are transmitted through the interface, used to control the detectors (Di) and detection elements ($D_{ijk}$) and for reading the signal from them, to a control and evaluation computer, in which they are analyzed for the purpose of reconstruction of a three-dimensional depiction of the spatial placement of the positron emitters in the source of the positrons in the investigated object, while the analysis concerns both, the coincidental events of registrations of the annihilation photons with energies in the interval from 507 keV to 513 keV to obtain the spatial depiction of the positions of positron annihilations, and the coincidental events of registrations of the annihilation photons with significantly Doppler shifted energies outside of that interval, which simultaneously fulfill the condition that the sum of the measured energies of these photons is, within the energy resolution of the affected detection elements ($D_{1jk}$) and ($D_{2jk}$), equal 1022 keV in CMS, which, according to the kinematics of positron annihilation, proves, that the positrons annihilated in flight closer to the position of the positron source, and thus allow to refine the positron source position determination in the investigated object initially obtained from the aforementioned spatial depiction of the positions of positron annihilations taking into account the annihilation photons with energies from 507 keV to 513 keV.

2. The method of improving the positron source position determination in an object investigated by the positron emission tomography according to claim 1 wherein the reconstruction of positions of the source of positrons in the object is performed using the kinematics of positron in flight annihilation with electrons on the basis of the measured energies of the individual pairs of concurrently occurring annihilation photons and of the coordinates of the positions of their registration in the affected detection elements ($D_{1jk}$) and ($D_{2jk}$) in the three-dimensional coordinate system according to the relativistic relations resulting from the energy and momentum conservation laws, $$\cos\theta = mc^2[(E_1+E_2)/E_1E_2]-1, \text{ where } E_1E_2=(¼)[(E_1+E_2)^2-(E_1-E_2)^2],$$

$$\cos\phi = (E_1-E_2\cos\theta)/[(E_1+E_2)(E_1+E_2-2mc^2)]^{1/2},$$

$$T_+ = E_1+E_2-2mc^2,$$

where $E_1$ and $E_2$ are the measured energies of photons resulting from annihilation of the positron with kinetic energy $T_+$ with an electron that was at rest or in thermal motion, that are influenced by the Doppler shift, where $E_1$ pertains to the photon with the Doppler shift towards higher energy, $E_2$ towards lower energy, the mc g gives the rest energy of the positron or electron, $p_+$ represents the momentum vector of the annihilating positron, $p_1$ and $p_2$ represent the momentum vectors of each annihilation photon from the pair, $\theta$ indicates the angle expressing the non-collinearity of those photons, $\phi$ the angle between the directions of vectors $p_1$ and $p_+$, while the position of positron annihilation in such an event is determined from the coordinates of the affected detection elements ($D_{1jk}$) and ($D_{2jk}$), which in coincidence measure $E_1$ and $E_2$ of the relevant annihilation photons, and the calculated values of $T_+$ and the angles $\theta$ and $\phi$.

3. The method of improving the positron source position determination in an object investigated by the positron emission tomography according to claim 1 wherein the positrons originating in the investigated object have energies greater than 10 keV.

4. The method of improving the positron source position determination in an object investigated by the positron emission tomography according to claim 1 wherein the source of positrons includes beta plus radionuclides with high energies of beta plus decay selected from the group of $^{22}$Na, $^{18}$F, $^{94}$Tc, $^{11}$C, $^{13}$N, $^{44}$Sc, $^{15}$O, $^{14}$O, $^{68}$Ga, $^{124}$I, $^{10}$C, $^{152}$Tb, $^{86}$Y, $^{76}$Br, $^{82}$Sr/$^{82}$Rb.

5. The method of improving the positron source position determination in an object investigated by the positron emission tomography according to claim 1 wherein the coincidental events of the registration of pairs of annihilation photons with significantly Doppler shifted energies have, for refining the depiction of the spatial distribution of positron sources in the investigated object, an increasingly greater weight once the Doppler shifts of the photon energies are increasingly greater.

6. The equipment for performing the method of improving the positron source position determination in an object investigated by the positron emission tomography according to claim 1 wherein it is consisting of a system of n position and energy-sensitive detectors ($D_i$) of gamma rays comprised of a system of detection elements ($D_{ijk}$), whose placement is described by a three-dimensional coordinate system, whereby the detection elements ($D_{ijk}$) are connected through an interface to computer used for controlling the detectors ($D_i$) and detection elements ($D_{ijk}$) and reading, analysis and evaluation of the signals from them with the purpose to reconstruct a three-dimensional depiction of the spatial distribution of the positron source in the investigated object.

7. The equipment for performing the method of improving the positron source position determination in an object investigated by the positron emission tomography according to claim 6 is wherein the energy-sensitive detectors ($D_i$) of gamma rays are hybrid pixel detectors with a pixel semiconductor sensor, while the system of pixels on them corresponds to the system of detection elements ($D_{ijk}$).

8. The equipment for performing the method of improving the positron source position determination in an object investigated by the positron emission tomography according to claim 7 is wherein the system of pixels on the hybrid pixel detectors, which corresponds to the system of detection elements ($D_{ijk}$), consists of pixels with 55 micrometers of size or smaller.

9. The equipment for performing the method of improving the positron source position determination in an object investigated by the positron emission tomography according to claim 6 is wherein the pixel semiconductor sensors of the hybrid pixel detectors are made from semiconductor materials with an effective atomic number $Z_{eff}$.

10. The equipment for performing the method of improving the positron source position determination in an object investigated by the positron emission tomography according to claim 9 is wherein the semiconductor materials with a high effective atomic number of $Z_{eff}$ are chosen from the group comprised of CdTe and CdZnTe.

11. The equipment for performing the method of improving the positron source position determination in an object investigated by the positron emission tomography according to claim 6 is wherein the interface for controlling the detectors ($D_i$) and detection elements ($D_{ijk}$) and for reading of the signal from them is chosen from the group of universal serial bus, Ethernet and PCI interfaces.

\* \* \* \* \*